US012776032B2

(12) United States Patent
Wick et al.

(10) Patent No.: US 12,776,032 B2
(45) Date of Patent: Oct. 27, 2026

(54) SYSTEMS AND METHODS FOR CO-REGISTERING IMAGERY OF DIFFERENT MODALITIES

(71) Applicants: CAMERAD TECHNOLOGIES, Decatur, GA (US); THE UAB RESEARCH FOUNDATION, Birmingham, AL (US)

(72) Inventors: Carson Arthur Wick, Decatur, GA (US); Srini Tridandapani, Decatur, GA (US); Pamela T. Bhatti, Decatur, GA (US)

(73) Assignee: Camerad Technologies, Decatur, GA (US)

( * ) Notice: Subject to any disclaimer, the term of this patent is extended or adjusted under 35 U.S.C. 154(b) by 512 days.

(21) Appl. No.: 18/345,326

(22) Filed: Jun. 30, 2023

(65) Prior Publication Data

US 2024/0013381 A1 Jan. 11, 2024

Related U.S. Application Data

(60) Provisional application No. 63/359,972, filed on Jul. 11, 2022.

(51) Int. Cl.
*G06T 7/00* (2017.01)
*A61B 6/00* (2024.01)
(Continued)

(52) U.S. Cl.
CPC .......... *G06T 7/0012* (2013.01); *A61B 6/5247* (2013.01); *G06T 7/11* (2017.01);
(Continued)

(58) Field of Classification Search
CPC ..... G06T 7/0012; G06T 7/174; A61B 6/5247; A61B 5/0035; A61B 8/5261
See application file for complete search history.

(56) References Cited

U.S. PATENT DOCUMENTS

2003/0026469 A1* 2/2003 Kreang-Arekul ...... G06V 10/24 382/132
2013/0034203 A1* 2/2013 Wang .................. A61B 6/5247 378/62
(Continued)

FOREIGN PATENT DOCUMENTS

CN 109934861 A * 6/2019

*Primary Examiner* — Molly Wilburn
(74) *Attorney, Agent, or Firm* — Workman Nydegger

(57) ABSTRACT

A method for co-registering imagery of different modalities includes accessing a first image captured according to a first imaging modality that depicts a plurality of physical markers. The plurality of physical markers is present within a scene represented in the first image. The method includes accessing a second image captured according to a second imaging modality that captures at least a portion of the scene including the plurality of physical markers. The method further includes generating a transformation matrix using the first image data and the second image data and generating an aligned image by applying the transformation matrix to the first image or the second image. The aligned image is combinable with the first image or the second image to generate co-registered image output. The co-registered image output depicts the portion of the scene according to the first imaging modality and the second imaging modality.

20 Claims, 14 Drawing Sheets

(51) Int. Cl.

| | |
|---|---|
| ***A61B 90/00*** | (2016.01) |
| ***G06T 7/11*** | (2017.01) |
| ***G06T 7/174*** | (2017.01) |
| ***G06T 7/33*** | (2017.01) |
| ***G06T 7/55*** | (2017.01) |
| ***G16H 30/20*** | (2018.01) |

(52) U.S. Cl.
CPC ................ *G06T 7/174* (2017.01); *G06T 7/33* (2017.01); *G06T 7/55* (2017.01); *G16H 30/20* (2018.01); *A61B 2090/3966* (2016.02); *G06T 2207/10116* (2013.01); *G06T 2207/30008* (2013.01); *G06T 2207/30204* (2013.01)

(56) References Cited

U.S. PATENT DOCUMENTS

| | | | | |
|---|---|---|---|---|
| 2017/0287184 | A1* | 10/2017 | Pettersson | G06F 18/22 |
| 2020/0219255 | A1* | 7/2020 | Wick | G06T 7/0012 |
| 2021/0228284 | A1* | 7/2021 | Voigt | A61B 34/20 |

* cited by examiner

1102

1100

SYSTEMS AND METHODS FOR CO-REGISTERING IMAGERY OF DIFFERENT MODALITIES

CROSS-REFERENCE TO RELATED APPLICATIONS

This application claims priority to U.S. Provisional Patent Application No. 63/359,972, filed on Jul. 11, 2022, and entitled "SYSTEMS AND METHODS FOR CO-REGISTERING IMAGERY OF DIFFERENT MODALITIES", the entirety of which is incorporated herein by reference.

STATEMENT REGARDING FEDERALLY SPONSORED RESEARCH

The invention was made with government support under 1853142 awarded by the National Science Foundation. The government has certain rights in the invention.

BACKGROUND

Advances in computing technology have resulted in a concomitant advance in medical device technologies, including within the field of diagnostic medicine. Particularly, the past century has demonstrated significant advances in medical imaging devices. Such advances have been hallmarked by the improvement and advent of new radiologic devices, such as radiography, computed tomography (CT), magnetic resonance imaging (MRI), and other radiologic imaging systems that allow for the non-invasive viewing and exploration of internal structures of the body. These medical imaging technologies allow physicians and clinicians to better document, diagnose, and treat pathologies.

Although many medical imaging devices are able to capture representations of internal bodily structures of patients, medical imaging devices may at times inadvertently capture structures that are external to bodily structures of patients. For example, many patients undergo medical imaging while external devices or instruments (e.g., tubes, lines, etc.) are positioned on or proximate to the patient's body (e.g., over or under the patient's clothing). Such external devices or instruments may be partially radiopaque or otherwise detectable by the medical imaging device. Accordingly, representations of the external devices or instruments may be depicted in the medical imagery captured for the patient (e.g., CT scans).

The inclusion of external structures within medical imagery can present problems for persons tasked with interpreting medical imagery. For example, a radiologist may be presented with a radiograph that includes depictions of external devices/instruments in combination with depictions of internal bodily structures and internal devices/instruments (e.g., pacemakers, catheters, breathing tubes, feeding tubes, etc.) of the imaged patient. This presents a risk that the radiologist may improperly interpret depictions of external devices or instruments within the radiograph as internal devices or instruments. For example, a radiologist may inadvertently interpret a depiction of an external tube as the internal portion of a feeding tube. Radiologists may similarly improperly interpret internal devices/instruments as external devices/instruments.

Such improper characterizations of structures represented within medical imagery can lead to errors in medical image interpretation, inefficiency in medical image interpretation (e.g., a radiologist may seek medical record information for the patient to better interpret the structures represented in the radiograph, which can occupy valuable time), and even lead to improper patient care decisions.

Accordingly, there is a need to reduce errors and/or inefficiencies in interpretation of medical imagery.

The subject matter described herein is not limited to embodiments that solve any disadvantages or that operate only in environments such as those described above. Rather, this background is only provided to illustrate one exemplary technology area where some embodiments described herein may be practiced.

BRIEF SUMMARY

Disclosed embodiments are directed to systems, devices, and methods for co-registering images of different modalities.

In one aspect, a computer-implemented method for co-registering simultaneously acquired imagery of different modalities includes accessing a first image captured according to a first imaging modality. The first image includes first image data depicting one or more physical markers according to the first imaging modality. The one or more physical markers are present within a scene represented in the first image. The method further includes accessing a second image captured according to a second imaging modality. The second image captures at least a portion of the scene represented in the first image including the one or more physical markers. The second image comprises second image data depicting the one or more physical markers according to the second imaging modality. The method further includes generating a transformation matrix using the first image data and the second image data and generating an aligned image by applying the transformation matrix to the first image or the second image. The aligned image is combinable with the first image or the second image to generate co-registered image output. The co-registered image output depicts the portion of the scene according to the first imaging modality and the second imaging modality.

In one aspect, a computer-implemented method for co-registering imagery of different modalities includes accessing a first image captured according to a first imaging modality. The first image comprises first image data depicting a representation of an image capture boundary of a second image sensor system associated with a second imaging modality. The representation of the image capture boundary is emitted by the second image sensor system onto a scene represented in the first image. The method further includes accessing a second image captured by the second image sensor system according to the second imaging modality and according to the image capture boundary. The method further includes using the representation of the image capture boundary as depicted in the first image to align the second image with the first image.

In one aspect, a computer-implemented method for facilitating co-registration of imagery of different modalities includes obtaining an expected overlap region. The expected overlap region comprises a region of a first image of a first imaging modality that is expected to depict one or more portions of a scene that are also depicted in a second image of a second imaging modality. The method also includes aligning the second image with the first image using first image data within the region of the first image and second image data of the second image. Aligning the second image with the first image refrains from utilizing image data of the first image that are outside of the region of the first image.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims or may be learned by the practice of the invention as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which.

DETAILED DESCRIPTION

Figure 1:
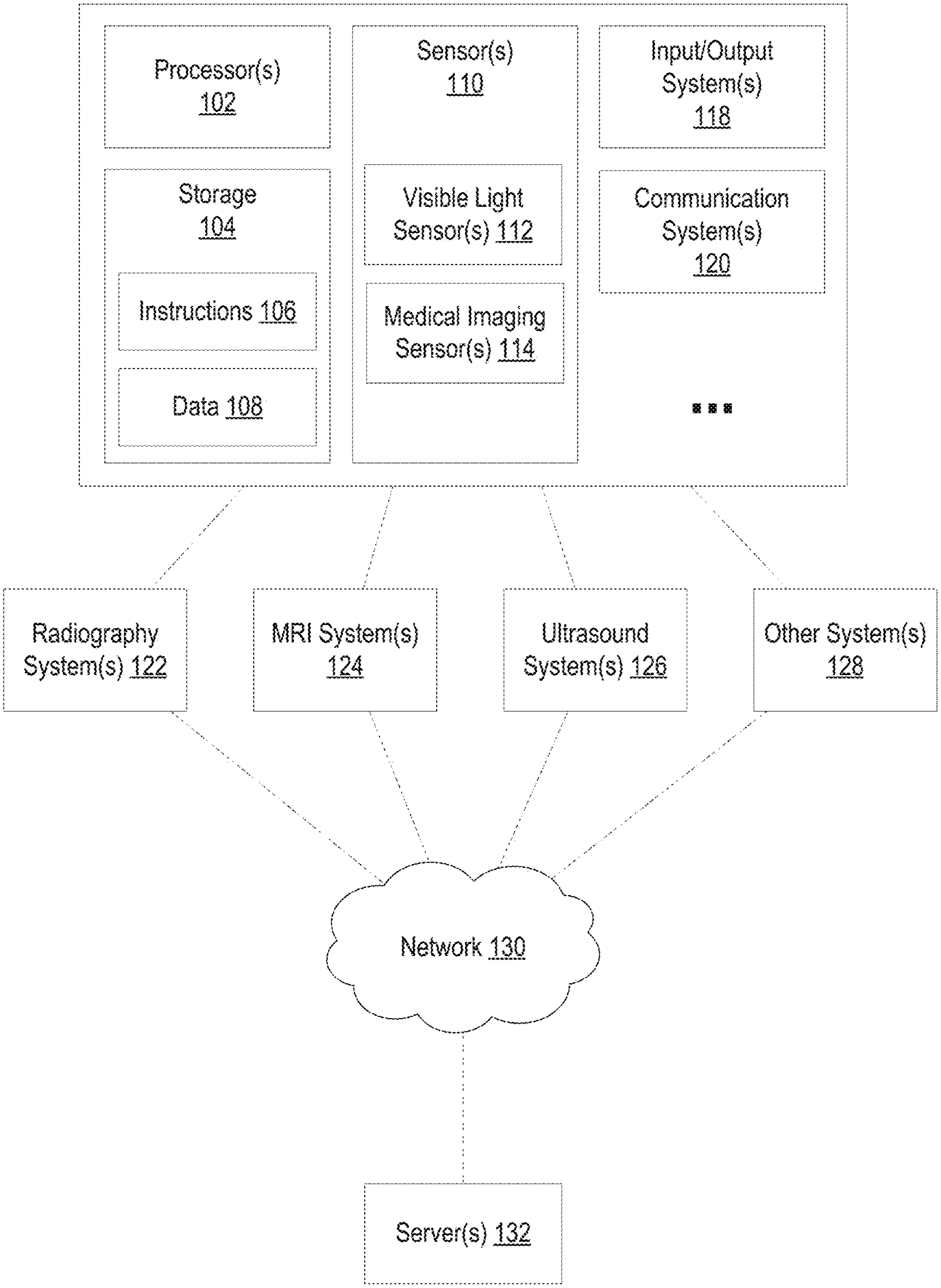
FIG. 1 illustrates example components of example systems that may comprise or implement the disclosed embodiments.

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, the particular example terminology used herein is for the purpose of describing the embodiments and is not necessarily intended to limit the scope of the claimed invention.

As noted above, despite the numerous advances made in the field of medical imaging, errors can still arise in the interpretation of medical imagery, especially where medical imagery depicts (i) devices/instruments that are external to the patient's body and (ii) devices/instruments that are internal to the patient's body.

The present disclosure relates to systems, methods, and devices for co-registering imagery of different modalities. Co-registering comprises aligning and overlapping different images to cause the images to appear as though they were captured from the same image capture position and orientation. Often, co-registered images are blended together (e.g., by increasing transparency of at least one image and displaying the transparent image over the other image).

As will be described in more detail hereinafter, a visible light image (e.g., a still image and/or an image frame of a video) may be captured of a patient in combination with a medical image of the patient (e.g., a CT, X-ray, MRI, Ultrasound, or other type of medical image). Co-registering the visible light image with the medical image may allow an interpreter of the medical image to readily ascertain whether structures represented in the medical imagery are external or internal to the patient's body.

For example, a radiologist may readily ascertain from the visible light image that the patient had a feeding tube at the time of medical imaging and enable the radiologist to discern which portions of the feeding tube as depicted in the medical image are within and outside of the patient's body. The radiologist may thus be presented with relevant information for interpreting the medical imagery without having to parse through medical records for context. In some instances, in addition to improving efficiency, co-registration of medical and visible light imagery may reduce interpretation errors and may facilitate avoidance of improper patient care decisions.

The present disclosure includes various techniques for co-registering imagery of different modalities. Some techniques utilize physical markers that are detectable in both visible light images and medical images (e.g., radiopaque markers, which can be detected in both visible light imagery and radiography imagery). Representations of the physical markers in both the visible light imagery and the medical imagery can be used to generate a transformation matrix, and the transformation matrix can be used to align and co-register the visible light imagery and the medical imagery. In addition to providing a basis for generating the transformation matrix for facilitation co-registration of the images, the physical markers may advantageously serve additional purposes, such as indicating laterality, whether a patient is lying or upright, etc.

Some techniques utilize an image capture boundary associated with capture of the medical image as a basis for co-registering the visible light image with the medical image. For example, many radiograph imaging systems are configured to project light onto the imaging scene (e.g., onto the patient) that indicates the portion of the imaging scene that will be depicted in the acquired radiograph. The light projected by the radiograph imaging system often comprises visible light, the reflections of which can be detected in visible light imagery acquired of the imaging scene. Thus, the visible light image can include a depiction of the imaging boundary projected by the medical imaging system, and this depiction of the imaging boundary can be used to align the medical image with the visible light image.

Some techniques include determining an estimated portion of the visible light image that the medical image is expected to overlap with. For example, when (i) the offset between the medical imaging sensor and the visible light imaging sensor, (ii) the field of view of the image sensors, and/or (iii) the distance between the image sensor(s) and the imaging subject(s) is/are known, a region of the visible light image that is expected to capture the same portions of the scene as the medical image can be identified. This expected overlap region can be used to reduce the search space for facilitating image co-registration between the visible light image and the medical image, thereby improving computational efficiency.

Having just described some various high-level features and benefits of the disclosed embodiments, attention will now be directed to FIGS. 1 through 14. These Figures illustrate various conceptual representations, components, architectures, methods, and supporting illustrations related to the disclosed embodiments.

Example Systems and Techniques for Co-Registering Imagery of Different Modalities FIG. 1 illustrates example components of example systems that may comprise or implement the disclosed embodiments. For example, the components illustrated in FIG. 1 include processor(s) 102, storage 104, sensor(s) 110, input/output system(s) 118 (I/O system(s) 118), and communication system(s) 120. Although FIG. 1 illustrates particular components, one will appreciate, in view of the present disclosure, that systems for implementing the disclosed embodiments may comprise any number of additional or alternative components (as indicated by the ellipsis).

The processor(s) 102 may comprise one or more sets of electronic circuitries that include any number of logic units, registers, and/or control units to facilitate the execution of computer-interpretable instructions (e.g., instructions that form a computer program). Such computer-interpretable instructions may be stored within storage 104. The storage 104 may comprise physical system memory and may be volatile, non-volatile, or some combination thereof. Furthermore, storage 104 may comprise local storage, remote storage (e.g., accessible via communication system(s) 120 or otherwise), or some combination thereof. Additional details related to processors (e.g., processor(s) 102) and computer storage media (e.g., storage 104) will be provided hereinafter.

In some implementations, the processor(s) 102 may comprise or be configurable to execute any combination of software and/or hardware components that are operable to facilitate processing using machine learning models or other artificial intelligence-based structures/architectures. For example, processor(s) 102 may comprise and/or utilize hardware components or computer-executable instructions operable to carry out function blocks and/or processing layers configured in the form of, by way of non-limiting example, single-layer neural networks, feed forward neural networks, radial basis function networks, deep feed-forward networks, recurrent neural networks, long-short term memory (LSTM) networks, gated recurrent units, autoencoder neural networks, variational autoencoders, denoising autoencoders, sparse autoencoders, Markov chains, Hopfield neural networks, Boltzmann machine networks, restricted Boltzmann machine networks, deep belief networks, deep convolutional networks (or convolutional neural networks), deconvolutional neural networks, deep convolutional inverse graphics networks, generative adversarial networks, liquid state machines, extreme learning machines, echo state networks, deep residual networks, Kohonen networks, support vector machines, neural Turing machines, and/or others.

As will be described in more detail, the processor(s) 102 may be configured to execute instructions 106 stored within storage 104 to perform certain actions associated with co-registering images of different modalities. The actions may rely at least in part on data 108 stored on storage 104 in a volatile and/or non-volatile manner.

In some instances, the actions may rely at least in part on communication system(s) 120 for receiving data from remote system(s), which may include, for example, separate systems or devices, sensors, servers, cloud resources/services, and/or others. The communications system(s) 120 may comprise any combination of software or hardware components that are operable to facilitate communication between on-system components/devices and/or with off-system components/devices. For example, the communications system(s) 120 may comprise ports, buses, or other physical connection apparatuses for communicating with other devices/components. Additionally, or alternatively, the communications system(s) 120 may comprise systems/components operable to communicate wirelessly with external systems and/or devices through any suitable communication channel(s), such as, by way of non-limiting example, Bluetooth, ultra-wideband, WLAN, infrared communication, and/or others.

FIG. 1 illustrates that a system for implementing the disclosed embodiments may comprise or be in communication with I/O system(s) 118. I/O system(s) 118 may include any type of input or output device such as, by way of non-limiting example, a touch screen, a mouse, a keyboard, a controller, and/or others, without limitation. For example, the I/O system(s) 118 may include a display system that may comprise any number of display panels, optics, laser scanning display assemblies, and/or other components.

Furthermore, FIG. 1 illustrates that a system for implementing the disclosed embodiments may comprise or be in communication with sensor(s) 110. Sensor(s) 110 may comprise any device for capturing or measuring data representative of perceivable or detectable phenomena. By way of non-limiting example, the sensor(s) 110 may comprise one or more image sensors, microphones, thermometers, barometers, magnetometers, accelerometers, gyroscopes, and/or others. FIG. 1 indicates that various types of image sensors are within the scope of the present disclosure. For instance, FIG. 1 depicts that the sensor(s) 110 may comprise visible light sensor(s) 112 and medical imaging sensor(s) 114. Visible light sensor(s) 112 may comprise charge-coupled device (CCD) image sensors, complementary metal-oxide-semiconductor (CMOS) image sensors, single photon avalanche diode (SPAD) image sensors, and/or any other type of image sensor configured to detect photons within (but not limited to) at least a portion of the visible spectrum (e.g., between about 380 nm and about 750 nm) to capture imagery (e.g., intensity or grayscale images, RGB images, and/or others).

Medical imaging sensor(s) 114 may comprise any type of device for capturing images of patients within a medical use context (e.g., medical assessment/diagnostic purposes, treatment assessment purposes, etc.). Medical imaging sensor(s) 114 may include, by way of non-limiting example, radiography devices (e.g., x-ray devices, computed tomography (CT) devices, positron emission tomography (PET) devices, nuclear medicine imaging devices, and/or others), magnetic resonance imaging (MRI) devices, ultrasound devices, and/or others.

The components shown in FIG. 1 may be implemented in various types and/or combinations of systems/devices. For example, any number of the components discussed hereinabove with reference to FIG. 1 may be implemented in association with radiography system(s) 122, MRI system(s) 124, ultrasound system(s) 126, and/or other system(s) 128. For example, radiography system(s) 122 may be implemented in the form of a portable digital radiography (DR) machine, with visible light sensor(s) 112 coupled to (e.g., whether selectively connected to or integrally formed with) the medical imaging sensor(s) 114 components of the DR machine.

Figure 2:
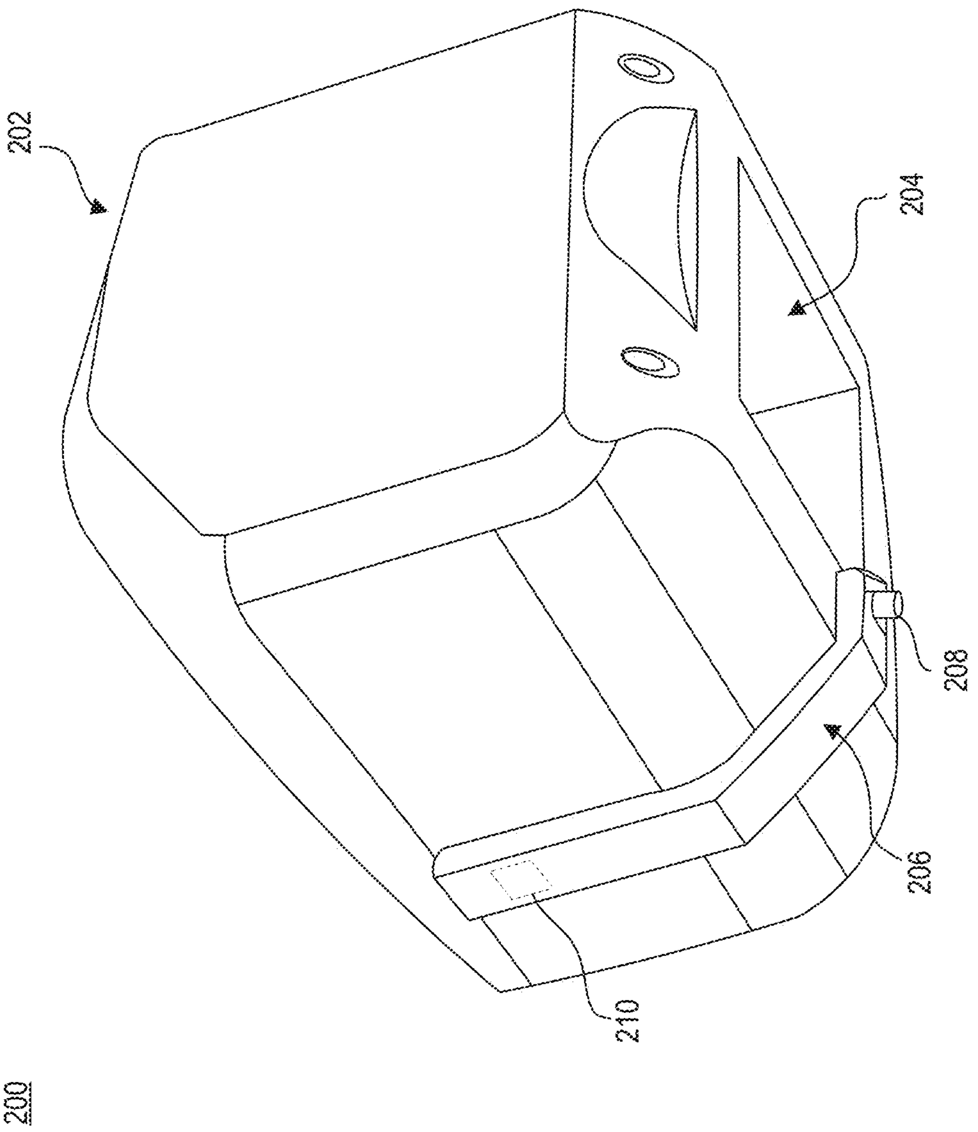
FIG. 2 illustrates an example visible light image sensor coupled to a medical image sensor.

Attention is briefly directed to FIG. 2, which illustrates an example isolated representation of an X-ray head 202 of a portable DR machine 200 (other components such as wires, handles, etc. are omitted for clarity). The portable DR machine 200 may comprise a radiography system 122 as discussed hereinabove with reference to FIG. 1. The X-ray head 202 includes an X-ray source 204 for emitting X-ray radiation to facilitate radiograph acquisition. The X-ray source 204 (combined with an X-ray detector) may comprise medical imaging sensor(s) 114 as described above with reference to FIG. 1. FIG. 2 also illustrates an example camera system 206 associated with the portable DR machine 200. The camera system 206 includes an image sensor 208 (e.g., visible light sensor(s) 112, discussed hereinabove with reference to FIG. 1) and a camera controller 210 (e.g., processor(s) 102 and/or storage 104, discussed hereinabove with reference to FIG. 1) to facilitate photograph and/or video acquisition.

FIG. 2 illustrates the camera system 206 is mounted or coupled to the X-ray head 202, thereby enabling easy use of the camera system 206 in conjunction with the X-ray head 202. For example, a medical imaging session may include capturing visible light images of a patient (utilizing the camera system 206) before, substantially contemporaneous with, or after capturing X-ray images of the patient (utilizing the X-ray source 204 and an X-ray detector). In this way, the X-ray head 202 and the camera system 206 may capture an imaging subject (e.g., a patient) with a substantially similar or identical pose or state.

One will appreciate, in view of the present disclosure, that visible light sensor(s) 112 may be mounted to, coupled with, or otherwise integrated into or associated with other types of medical imaging sensors, such as CT devices, MRI devices, ultrasound devices, etc.

Medical images (e.g., captured via the X-ray source 204 and an X-ray detector of the portable DR machine 200), visible light images (e.g., captured utilizing the camera system 206), and/or recorded audio acquired pursuant to a medical imaging session for a particular patient may be stored in association with the identity of the particular patient. For example, FIG. 1 shows that the radiography system(s) 122, the MRI system(s) 124, the ultrasound system(s) 126, and/or the other system(s) 128 may be in communication with a network 130. The network may comprise one or more links that enable the transport of information between and/or among systems, modules, and/or devices. FIG. 1 also illustrates server(s) 132 in communication with the network 130 and therefore in communication with the radiography system(s) 122, the MRI system(s) 124, the ultrasound system(s) 126, and/or the other system(s) 128. The server(s) 132 may comprise any of the components discussed hereinabove with reference to FIG. 1, such as processor(s) 102, storage 104, I/O system(s) 118, communication system(s) 120, etc.

The server(s) 132 may be configured to receive and store information from the radiography system(s) 122, the MRI system(s) 124, the ultrasound system(s) 126, and/or the other system(s) 128 in association with particular patients. The server(s) 132 may thus operate similar to a patient database and/or a picture archiving and communication system (PACS).

Various acts may be performed utilizing captured medical imagery and/or visible light imagery to facilitate generation of co-registered imagery (e.g., with the medical imagery and the visible light imagery spatially aligned such that objects in the captured scene that are depicted in both the medical imagery and the visible light imagery appear to overlap). Such acts may be performed utilizing any suitable computing system(s) or device(s) (e.g., utilizing processor(s) 102 and/or storage 104 of radiography system(s) 122, MRI system(s) 124, ultrasound system(s) 126, server(s) 132, other system(s) 128 (e.g., user workstations, mobile electronic devices, etc.).

Figure 3:
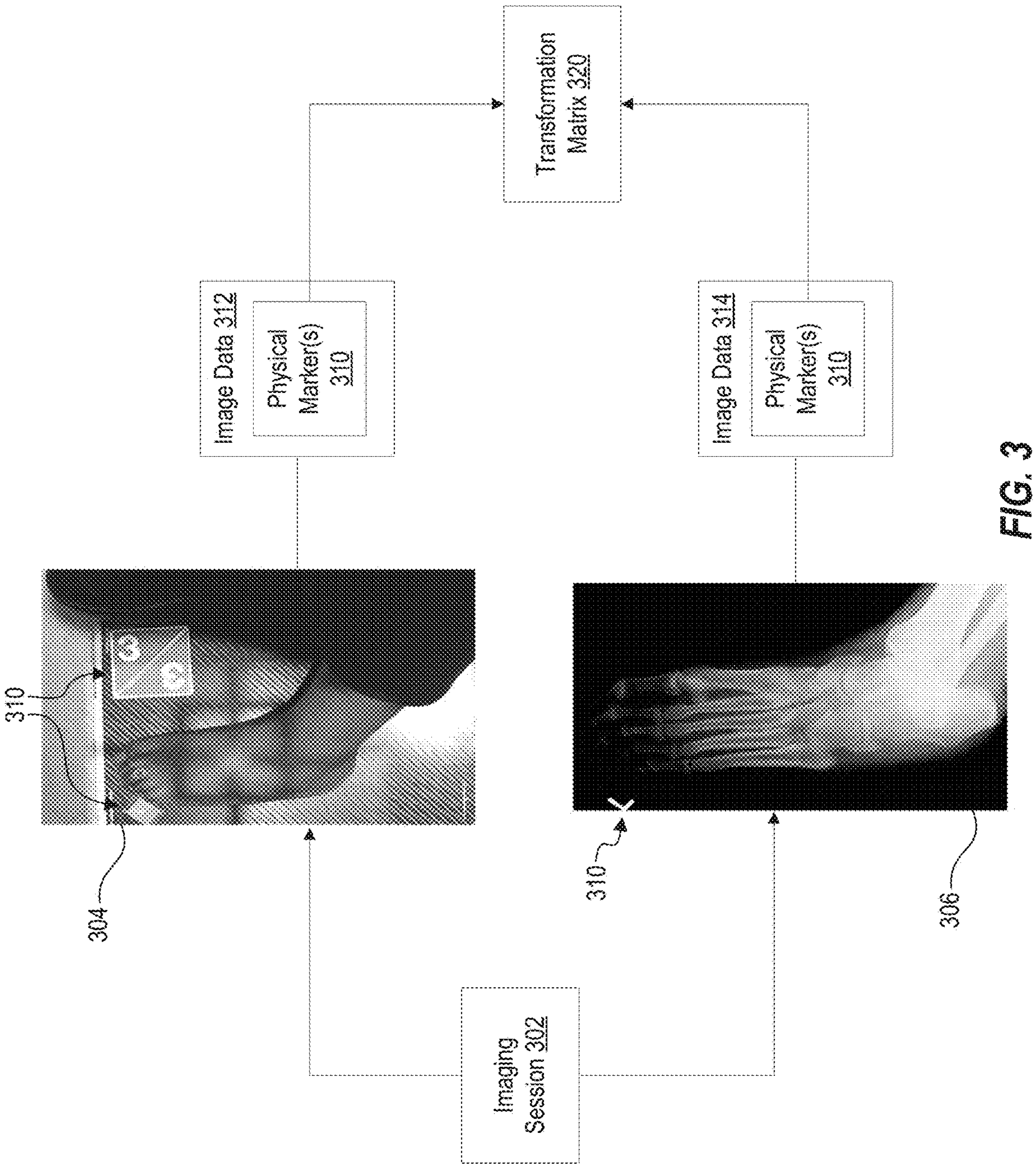
FIG. 3 illustrates an example conceptual representation of visible light imagery and medical imagery that include depictions of physical markers.

FIG. 3 illustrates an example conceptual representation of an imaging session 302. Pursuant to the imaging session 302, a technologist (or other person) may be tasked with acquiring medical imagery of an imaging subject (e.g., a medical patient). A technologist (or other person) may utilize any suitable imaging system(s) to acquire such imagery, such as a portable DR machine 200 with a camera system 206 attached thereto. The X-ray source 204 and X-ray detector may capture a medical image of the imaging subject, and the camera system 206 may capture a visible light image (and/or video) of the imaging subject.

Although the present disclosure focuses, in at least some respects, on utilizing a visible light imaging sensor and a medical imaging sensor (e.g., a radiograph image sensor) to capture images of imaging subjects for co-registration thereof, one will appreciate, in view of the present disclosure, that any two imaging modalities may be used in accordance with the principles described herein (e.g., visible light imagery and/or visible light image sensors may be regarded more generally as associated with a first imaging modality, and medical imagery and/or medical image sensors may be regarded more generally as associated with a second imaging modality).

FIG. 3 illustrates an example visible light image 304 and an example medical image 306 captured pursuant to the imaging session 302. The visible light image 304 of FIG. 3 captures external portions of the imaging subject (e.g., portions that are visible within the visible spectrum), and the medical image 306 of FIG. 3 captures internal portions of the imaging subject (e.g., portions that are visible outside of the visible spectrum or that are detectable by other means, such as X-ray, MRI or ultrasound). In the particular example of FIG. 3, the visible light image 304 depicts external portions of a patient's left foot, and the medical image 306 depicts radiographically internal portions of the patient's left foot.

Prior to acquiring the images pursuant to the imaging session 302, the technologist (or another entity) may arrange physical markers 310 within the imaging scene that includes the imaging subject. Physical markers 310 arranged within the captured scene are captured and depicted (along with the imaging subject) in both the visible light image 304 and the medical image 306 (one of the physical markers 310 is cropped from the medical image 306 of FIG. 3). The physical markers 310 may comprise a material or form that enables the physical markers 310 to be depicted in both the visible light imagery and the medical imagery. For example, the physical markers 310 may comprise radiopaque physical markers (e.g., lead markers) that are detectable in radiograph imaging and in visible light imaging.

As noted above, the physical markers 310 are depicted within the visible light image 304 and the medical image 306, which is further indicated in FIG. 3 by the image data 312 of the visible light image 304 comprising or representing the physical markers 310 and the image data 314 of the medical image 306 comprising or representing the physical markers 310. To facilitate co-registration of the visible light image 304 and the medical image 306, a system may generate a transformation matrix 320 utilizing the depictions of the physical markers 310 within the image data 312 of the visible light image 304 and the image data 314 of the medical image 306. The transformation matrix 320 may be configured to cause the representations of the physical markers 310 within the visible light image 304 and the medical image 306 to become overlapped or spatially aligned when the transformation matrix 320 is applied to the visible light image 304 and/or the medical image 306. In some instances, input for generating the transformation matrix 320 omits image data depicting portions of the images that do not depict the physical markers 310.

The transformation matrix 320 may take on various forms, such as translation, rotation, scaling, rigid transformation, similarity transformation, affine transformation, projective transformation, homographic transformation, and/or others. One or more corresponding portions of the image data 312 and the image data 314 that depict the physical markers 310 may be treated as feature matches for the purpose of generating the transformation matrix 320. The transformation matrix 320 may thus be computed to indicate transformative operations that may be applied to the visible light image 304 and the medical image 306 to cause substantial spatial alignment of the corresponding depictions of the physical markers 310 in the image data 312 and 314 (e.g., via least squares techniques, random sample consensus techniques, deep learning or other artificial intelligence-based techniques, and/or other techniques). It will be appreciated that the computation of the transformation matrix 320 may comprise any number of iterations. The transformation matrix 320 may be computed according to any desirable frame of reference (e.g., using the visible light image as a reference such that the transformation matrix 320 is configured to align the medical image with the visible light image, or vice versa, or utilizing a different frame of reference).

Figure 4:
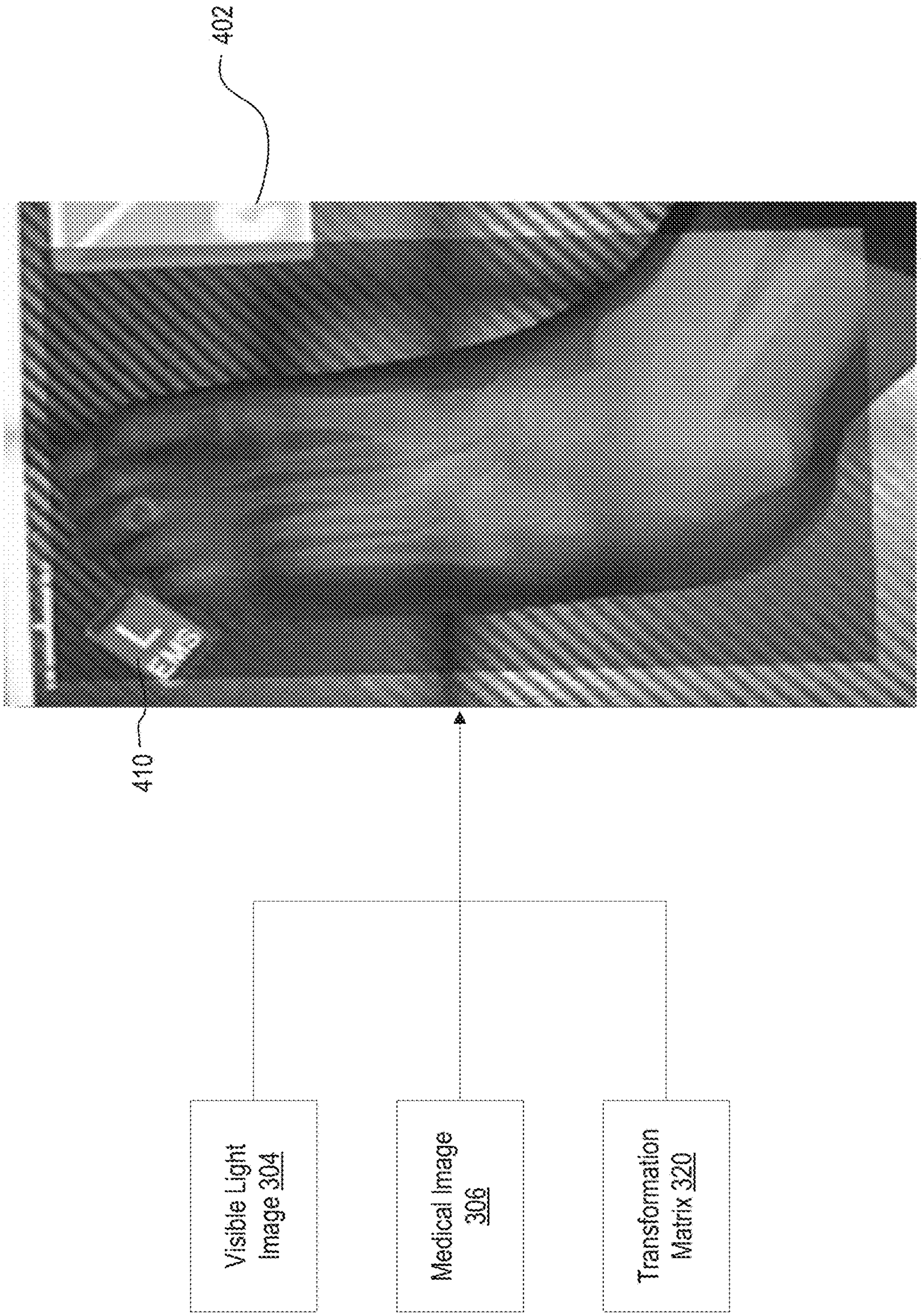
FIG. 4 illustrates a conceptual representation of generating a co-registered image based upon visible light imagery and medical imagery using a transformation matrix.

FIG. 4 illustrates a conceptual representation of generating a co-registered image 402 based upon the visible light image 304, the medical image 306, and the transformation matrix 320 of FIG. 3 as discussed above. After image acquisition pursuant to the imaging session 302 of FIG. 3, the visible light image 304 and the medical image 306 that depict the physical markers 310 may be accessed. The transformation matrix 320 may be generated utilizing as feature matches the corresponding depictions of the physical markers 310 in the visible light image 304 and the medical image 306. The transformation matrix 320 may then be applied to at least a portion of the visible light image 304 and/or the medical image 306 to cause the corresponding depictions of the physical markers 310 in the visible light image 304 and the medical image 306 to spatially overlap or become spatially aligned (as indicated in FIG. 4, illustrating the spatially overlapping physical markers 410). Such spatial alignment facilitated by application of the transformation matrix 320 may cause other portions of the visible light image 304 and the medical image 306 to become spatially aligned.

The transformed or spatially aligned visible light image and medical image may be displayed in conjunction with one another (or composited or combined), thereby providing a co-registered image 402. The co-registered image 402 of FIG. 4 advantageously depicts portions of the imaging subject (e.g., the patient's left foot) according to the visible light imaging modality and the medical imaging modality (e.g., X-ray). The co-registered image 402 may be presented on a user interface, such as to enable improved and/or efficient interpretation of the imaging study performed for the patient.

Although portions of the present description may refer to physical markers in the plural form, it will be appreciated, in view of the present disclosure, that one or more physical markers may be utilized in accordance with the principles described herein. For instance, a single physical marker may comprise multiple components that may be used to generate a transformation matrix when captured according to different imaging modalities (e.g., a circumferential radiopaque marker configured to be positioned about a patient's bodily structure that is queued for imaging).

In some instances, the physical marker(s) perform additional functions in addition to providing a feature matching bases for generating a transformation matrix to facilitate generation of co-registered imagery. For instance, in the examples of FIGS. 3 and 4, at least some of the physical markers 310 indicate laterality of the portion of the imaging subject that is subjected to medical and visible light imaging in accordance with the imaging session 302 (e.g., the physical markers 310 of FIG. 3 depict an "L" representative of the left side of a patient's body).

Figure 5B:
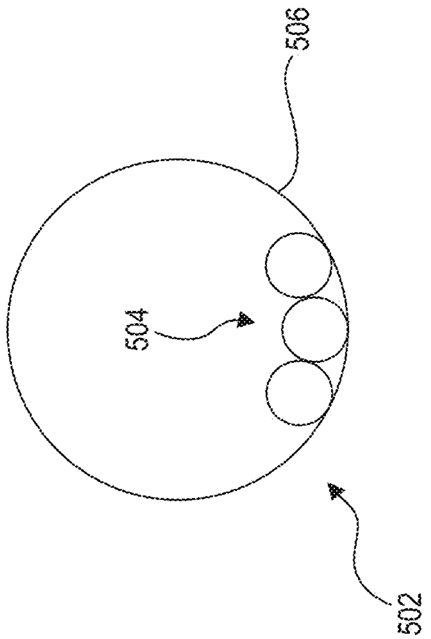
FIGS. 5A and 5B illustrate an example physical marker that may be captured by both visible light image sensors and medical image sensors.
Figure 5A:
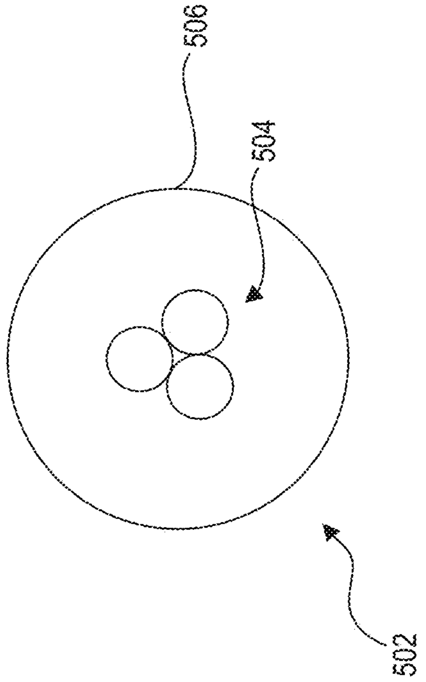

The physical marker(s) may, in some implementations, perform functions in addition to or as an alternative to those discussed above with reference to the physical markers 310 of FIG. 3. For example, FIGS. 5A and 5B illustrate an example of a physical marker 502 that may be captured by both visible light image sensors and medical image sensors. The physical marker 502 may comprise free-moving components, such as lead beads 504 enclosed within an at least partially curved transparent enclosure 506. The lead beads 504 may be configured to assume different positions based upon the position or orientation of the physical marker 502. For instance, when the physical marker 502 is horizontally positioned adjacent to a patient who is lying down, the lead beads 504 may roll into a cluster centrally positioned on a curved face of the transparent enclosure 506, as depicted in FIG. 5A. Thus, when the physical marker 502 is captured as shown in FIG. 5A in combination with an imaging subject who is lying down, the physical marker 502 may indicate in the captured imagery that the patient was in a lying position during acquisition of the imagery. In contrast, when the physical marker 502 is vertically positioned adjacent to a patient who is in an upright position, the lead beads 504 may roll into arrangement toward the bottom of the enclosure 506, as depicted in FIG. 5B. Thus, when the physical marker 502 is captured as shown in FIG. 5B in combination with an imaging subject who is in an upright position, the physical marker 502 may indicate in the captured imagery that the patient was in an upright position during acquisition of the imagery.

In view of the foregoing, the physical marker(s) captured to facilitate generation of a transformation matrix for forming co-registered imagery may indicate imaging subject laterality, imaging subject orientation, and/or other aspects of the imaging session and/or imaging subject.

Additional or alternative techniques may be employed to facilitate generation of co-registered imagery, in accordance with the present disclosure. In some instances, medical imaging systems (e.g., portable DR machine 200 of FIG. 2) are configured to project or emit visible light onto an imaging scene (e.g., onto at least a portion of an imaging subject) that indicates the field of view of the medical imaging system. The portions of the scene illuminated by the emitted visible light may be expected to be represented in medical imagery captured by the medical imaging system. Such functionality may assist technologists in positioning imaging subjects for medical image acquisition.

Figure 6:
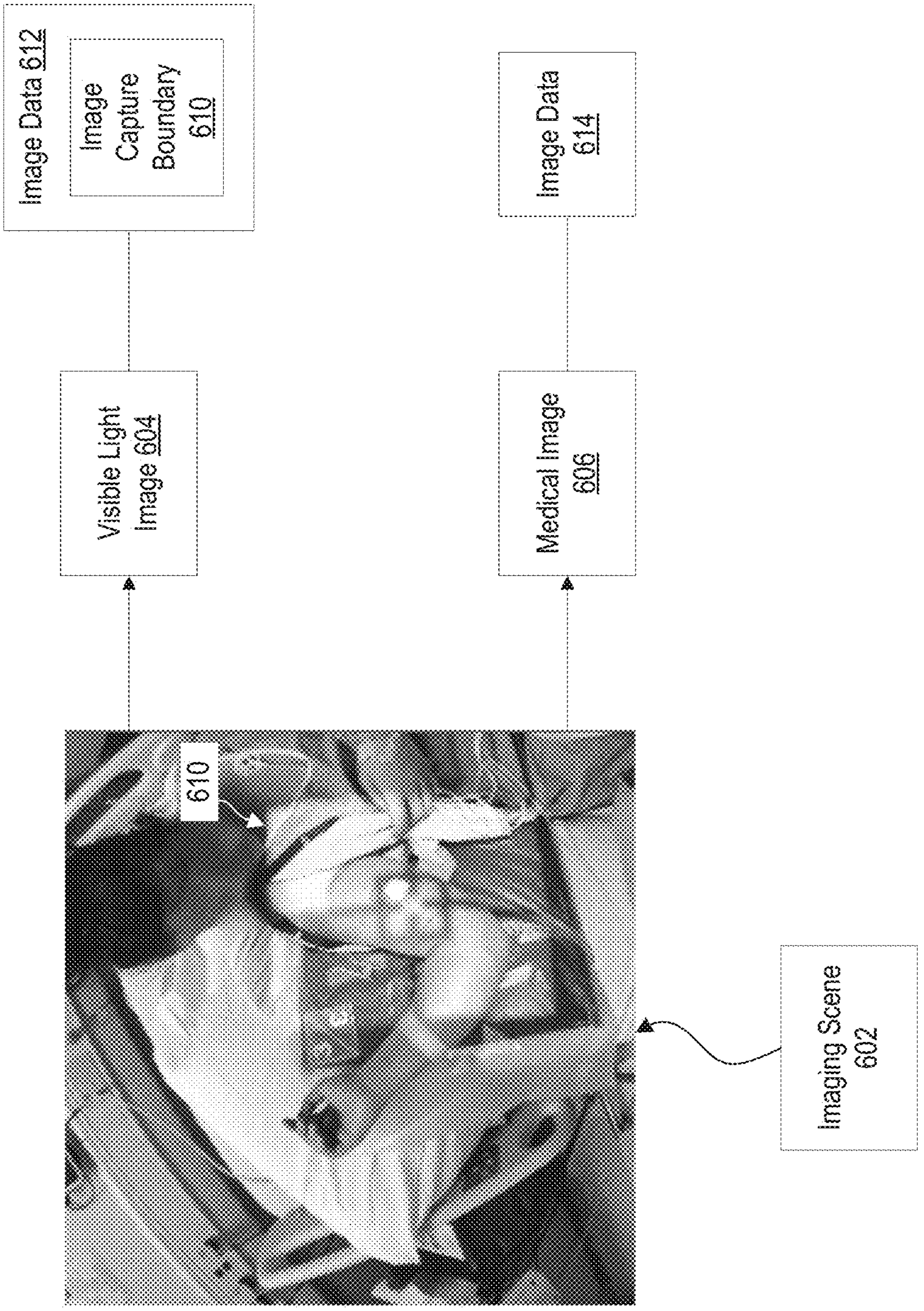
FIG. 6 illustrates an example conceptual representation of visible light imagery that depicts an image capture boundary projected by a medical imaging system.

For example, FIG. 6 illustrates an example conceptual representation of an imaging scene 602 onto which an imaging capture boundary 610 is projected by a medical imaging system (e.g., such as a portable DR machine 200). As noted above, the image capture boundary 610 of the medical imaging system projected onto the imaging scene 602 may comprise visible light emitted by the medical imaging system and may therefore be depicted in visible light imagery captured of the imaging scene 602. Thus, the example of FIG. 6 shows a visible light image 604 captured of the imaging scene 602 that includes image data 612 depicting the representation of the image capture boundary 610 that was projected onto the imaging scene 602 by the medical imaging system. FIG. 6 additionally shows a medical image 606 captured of the imaging scene 602 that includes associated image data 614.

Figure 7:
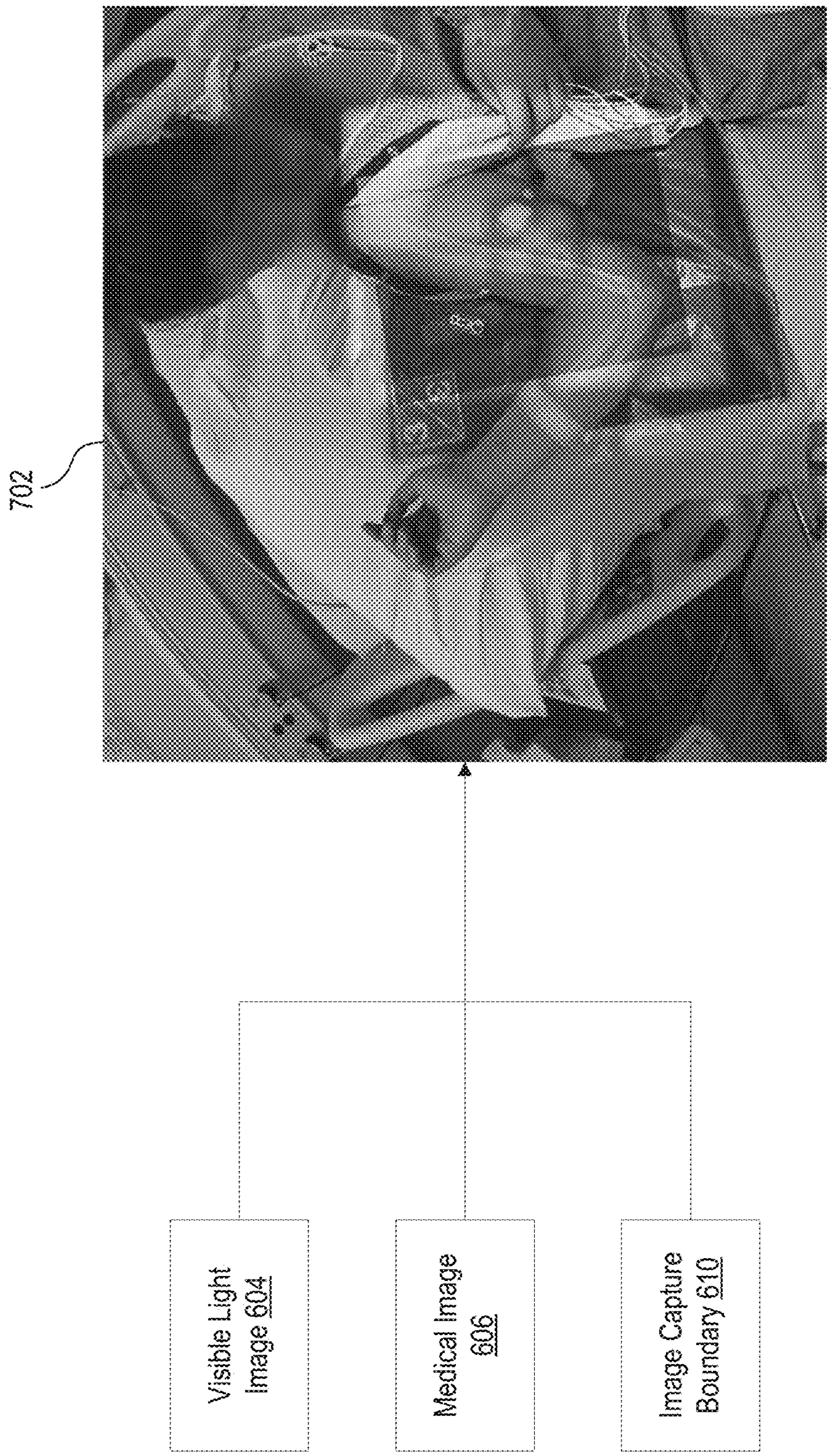
FIG. 7 illustrates a conceptual representation of generating a co-registered image based upon visible light imagery and medical imagery using an image capture boundary depicted in the visible light imagery.

The image capture boundary 610 depicted in the image data 612 of the visible light image 604 may be used to align the visible light image 604 with the medical image 606 (e.g., to provide co-registered image output). FIG. 7 illustrates a conceptual representation of generating a co-registered image 702 based upon the visible light image 604 and the medical image 606 using the image capture boundary 610 depicted in the visible light image 604. The image capture boundary 610 may be used to align the medical image 606 with the visible light image 604 in various ways. For example, in some implementations, the image capture boundary 610 coincides with the boundary of medical imagery captured by the medical imaging system that projected the image capture boundary 610 onto the imaging scene 602. Thus, in some implementations, the medical image 606 may be transformed to cause the boundary of the medical image 606 to align with the representation of the outer edges of the image capture boundary 610 shown in the visible light image 604. For instance, a transformation matrix may be calculated that maximizes or optimizes the overlap between the outer boundary of the medical image 606 and the depiction of the image capture boundary 610 present in the visible light image 604.

In some implementations, the image capture boundary 610 provides for a reduction in the search space within which image data is processed to facilitate alignment of the visible light image 604 and the medical image 606. For instance, the representation of the image capture boundary 610 in the visible light image 604 may be used to bound the image data of the visible light image 604 that is used as input to detect representations of physical markers (as discussed above) and/or other features that correspond between the visible light image 604 and the medical image 606 (e.g., to be used as feature matches to generate a transformation matrix for providing a co-registered image). As another example, the representation of the image capture boundary 610 in the visible light image 604 may be used to bound the image data of the visible light image 604 that is used to maximize mutual information between the visible light image 604 and the medical image 606. A system may therefore refrain from processing image data outside of the boundary established in the visible light image 604 by the image capture boundary 610, thereby improving computational efficiency in generating co-registered imagery.

Figure 8:
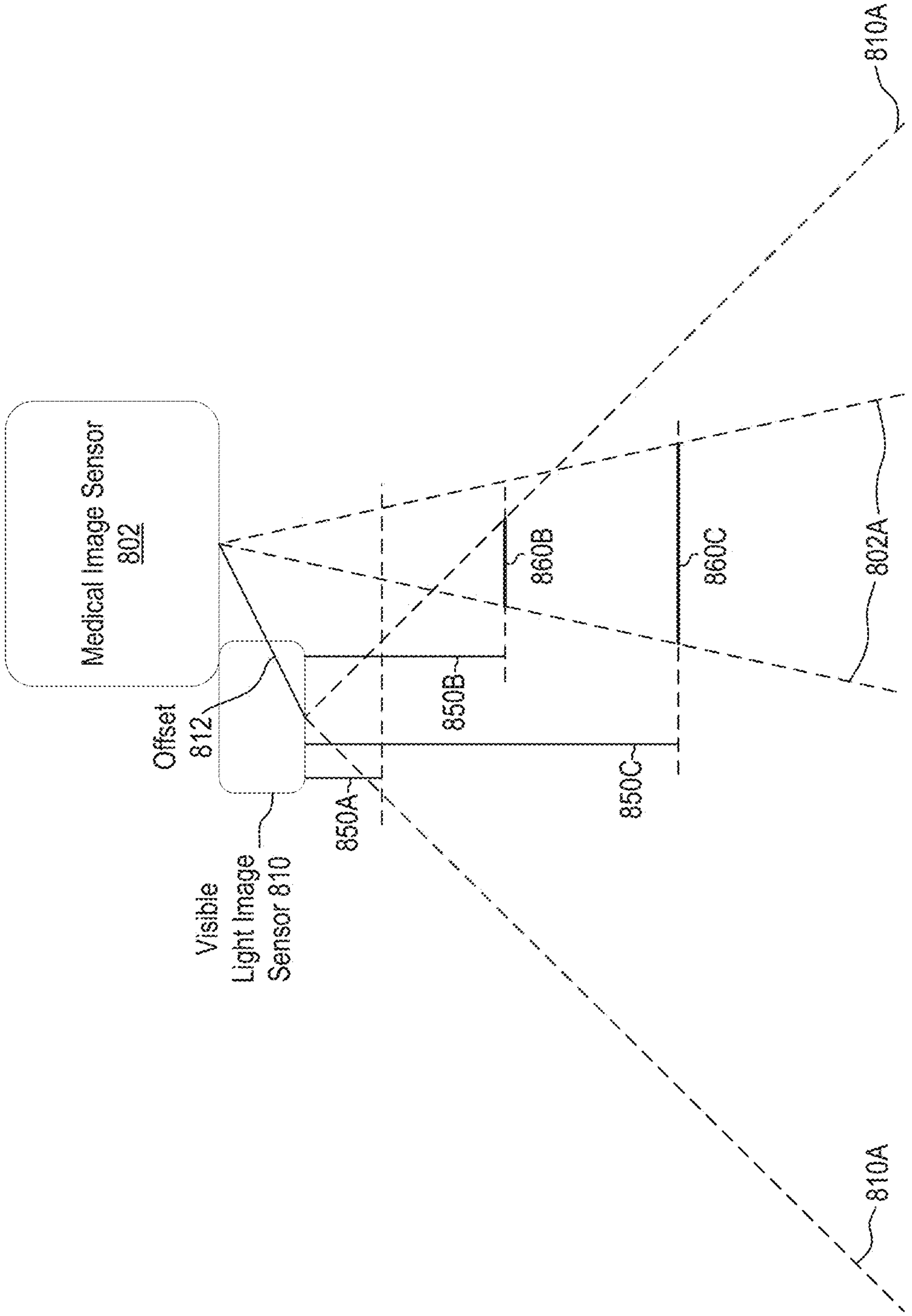
FIG. 8 illustrates a conceptual example of an expected overlap region where a medical image sensor and a visible light image sensor are expected to capture the same portions of an imaging scene.

Additional or alternative information or data may be utilized to provide for a reduction in the search space within which image data is processed to facilitate alignment of visible light imagery with medical imagery. For instance, FIG. 8 illustrates an example schematic layout of a medical image sensor 802 and a visible light image sensor 810. By way of illustrative example, the medical image sensor 802 may correspond to an X-ray head 202 of a portable DR machine 200, and the visible light image sensor 810 may correspond to a camera system 206 affixed to the medical image sensor 802.

FIG. 8 illustrates an offset 812 between the medical image sensor 802 and the visible light image sensor 810. This offset 812 may comprise various components and may be represented in various ways (e.g., an x-offset (horizontal), a y-offset (vertical), a z-offset (depth)). The offset 812 may provide a basis for estimating an expected overlap region that can be used to reduce the image data of visible light imagery that is used to facilitate co-registration between the visible light imagery captured by the visible light image sensor 810 and medical imagery captured by the medical image sensor 802.

FIG. 8 depicts a field of view 810A associated with the visible light image sensor 810 and a field of view 802A associated with the medical image sensor. As is shown in FIG. 8, the fields of view 810A and 802A overlap through at least a portion of the imaging scene. The offset 812 and the fields of view 810A and 802A may be used to determine an expected overlap region within visible light imagery captured by the visible light image sensor 810 that is expected to depict portions of the imaging scene that are also depicted in medical imagery captured by the medical image sensor 802. For example, the region of a visible light image captured by the visible light image sensor 810 that is expected to overlap with a medical image captured by the medical image sensor 802 may be affected by the distance between the image sensors and the objects in the scene. This is evident in the example of FIG. 8, where objects positioned very close to the image sensors (e.g., at depth 850A) could be captured by the medical image sensor 802 or the visible light image sensor 810, but not both, where objects positioned at an intermediate depth from the image sensors (e.g., at depth 850B) may be captured by both the medical image sensor 802 and the visible light image sensor 810 within a small region (e.g., region 860B), and where objects positioned at a greater depth from the image sensors (e.g., at depth 850C) may be captured by both the medical image sensor 802 and the visible light image sensor 810 within a larger region (e.g., region 860C).

Figure 9:
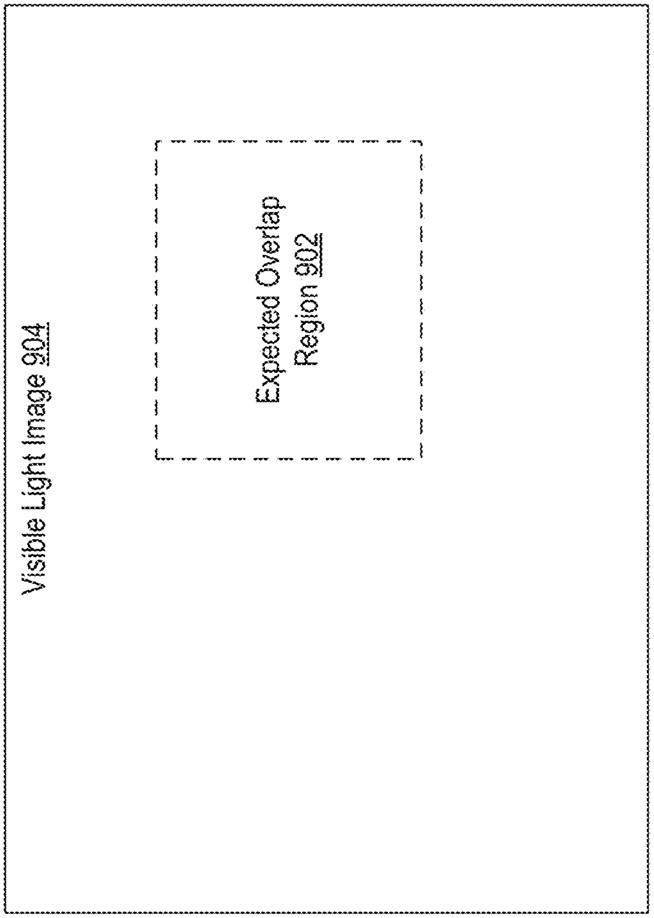
FIG. 9 illustrates a conceptual depiction of an expected overlap region within a visible light image.

Accordingly, depth information (or expected depth information) indicating a distance between the medical image sensor 802 and/or the visible light image sensor 810 and one or more objects to be captured by the medical image sensor 802 and the visible light image sensor 810 may be used in combination with the offset 812 and/or the fields of view 802A and 810A to determine an expected overlap region. FIG. 9 depicts an example visible light image 904 captured by the visible light image sensor 810 and an expected overlap region 902 within which both the visible light imagery and medical imagery are expected to capture the same portions of the imaged scene.

The depth information used to define the overlap region 902 may be obtained or determined in various ways. For example, in some implementations, imaging specifications or image acquisition protocols associated with the medical image sensor 802 (and/or the visible light image sensor 810) may indicate a predetermined maximum depth, minimum depth, and/or range of depths from which the medical image sensor 802 (and/or the visible light image sensor 810) is adapted to acquire images of objects. Such predetermined depth information (e.g., maximum depth) may be utilized in combination with field of view information and/or offset information to determine the expected overlap region 902. In some instances, the depth information used to define the overlap region is dynamically acquired by one or more depth detection systems associated with the medical image sensor 802 and/or the visible light image sensor (e.g., via stereo cameras, time-of-flight sensor(s), range finder(s), etc.). The depth information may be based upon imaging convention established by an entity that controls medical image acquisition (e.g., a hospital, medical clinic, regulatory body, etc.).

The example of FIG. 9 depicts the expected overlap region 902 as a subset of the visible light image 904, in particular because the visible light image sensor 810 of FIG. 8 comprises a wider field of view than the medical image sensor 802. It will be appreciated, in view of the present disclosure, that an expected overlap region may be defined as a subset of a medical image that is expected to capture portions of an imaged environment that are also captured by a visible light image.

Although the examples discussed with reference to FIGS. 8 and 9 indicate use of an offset 812 to assist in determining the expected overlap region 902, the medical image sensor 802 and the visible light image sensor 810 may be co-located (or assumed co-located) in one or more dimensions in accordance with the present disclosure.

Figure 10:
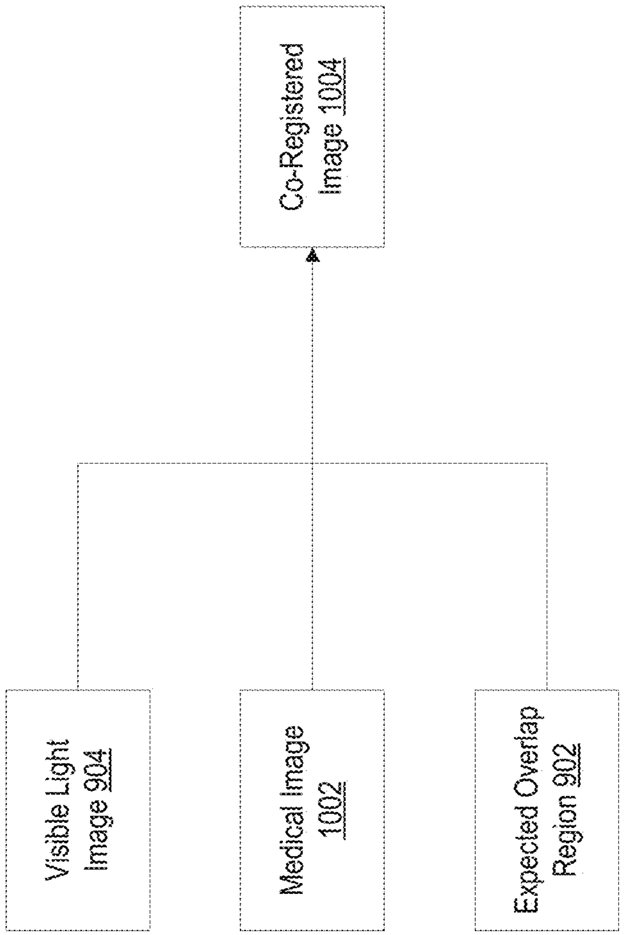
FIG. 10 illustrates a conceptual representation of generating a co-registered image based upon visible light imagery and medical imagery using an expected overlap region.

FIG. 10 illustrates a conceptual representation of generating a co-registered image 1004 based upon a visible light image (e.g., captured by the visible light image sensor 810), a medical image 1002 (e.g., captured by the medical image sensor 802) and the expected overlap region 902 (e.g., determined utilizing field of view information, depth information, and/or offset information associated with the medical image sensor 802 and/or the visible light image sensor 810). The expected overlap region 902 may be used to align the medical image 1002 with the visible light image 904 to generate the co-registered image 1004, such as by reducing a search space within the visible light image 904 within which to search for corresponding structures between the visible light image 904 and the medical image 1002 for generating a transformation matrix for aligning the visible light image 904 and the medical image 1002. The corresponding structures may, in some instances, comprise physical markers (e.g., physical markers 310) placed within an imaged scene in preparation for an imaging session of an imaging subject (e.g., a patient). In some instances, the physical markers comprise one or more medical components associated with an imaging subject (e.g., a patient) that are detectable in medical imaging and visible light imaging.

In some instances, a system may align the medical image 1002 with the visible light image 904 by maximizing mutual information between the medical image 1002 and the expected overlap region or reduced search space of the visible light image 904. Systems may advantageously refrain from utilizing image data of the visible light image 904 that is outside of the expected overlap region and focus on the reduced search space of the visible light image 904 to facilitate aligning of the visible light image 904 with the medical image 1002 to form a co-registered image 1004.

Figure 11:
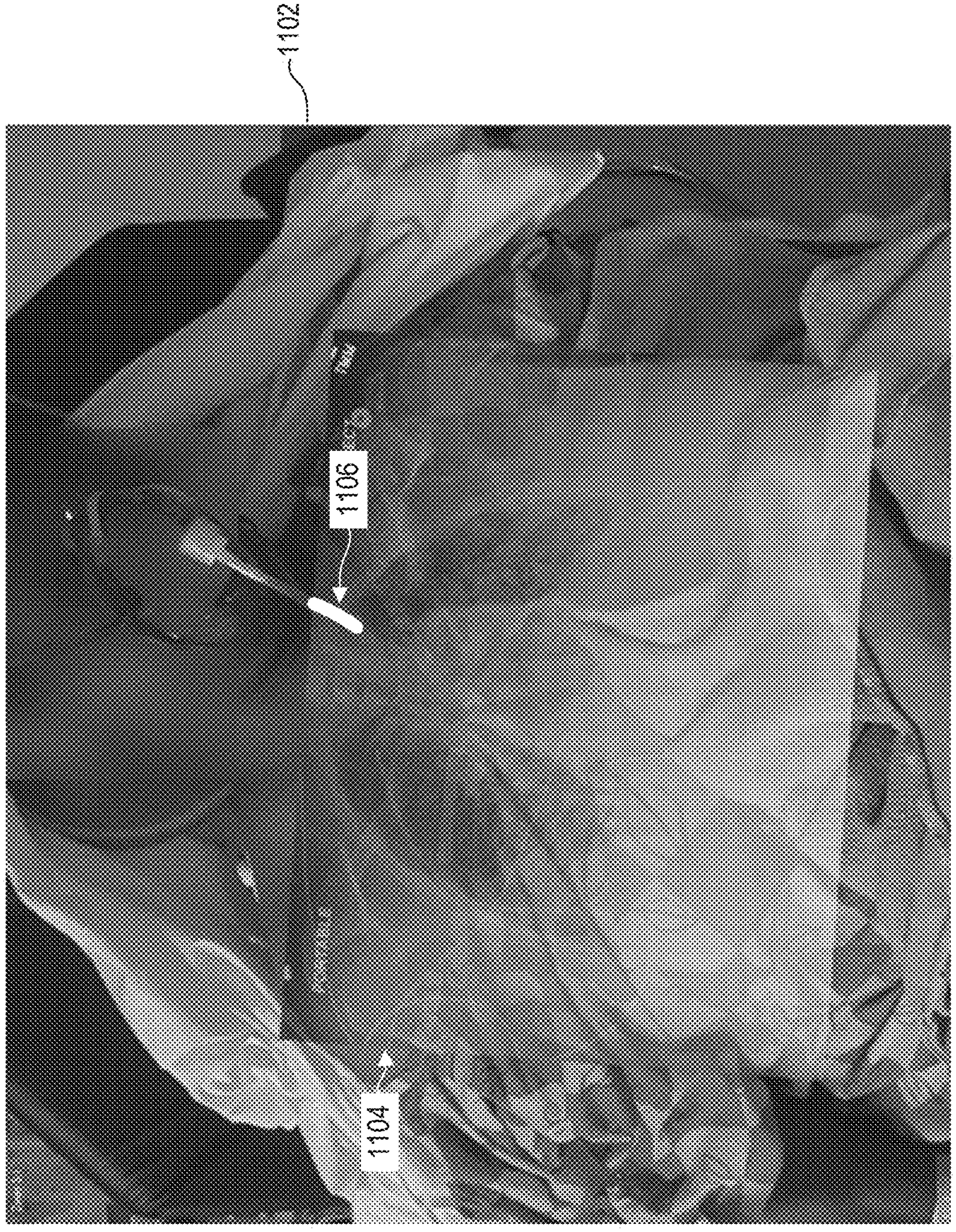
FIG. 11 illustrates an example co-registered image with a portion of the co-registered image emphasized to indicate a structure that is depicted in both the visible light image and the medical image.

FIG. 11 illustrates an example co-registered image 1100 formed from a visible light image 1102 and a medical image 1104. FIG. 11 illustrates a portion 1106 of the co-registered image 1100 highlighted or emphasized to indicate a structure that is depicted in both the visible light image 1102 and the medical image 1104. The portion 1106 may represent spatially overlapped visible light image and medical image representations of the structure in the co-registered image 1100. The structure may comprise physical markers, medical components, and/or other materials that are detectable under both visible light imaging and medical imaging. The portion 1106 may be automatically or selectively highlighted or emphasized within the presentation of the co-registered image responsive to user input or upon generation of the co-registered image. Such functionality may enable users to readily interpret aspects of medical imagery (e.g., by allowing users to determine which portions of a medical image were also detected under visible light imaging, thereby indicating that the portions are external or on the surface of the patient's body). In some instances, a user may provide input during presentation of a co-registered image 1100 to modify the prevalence of the visible light image content and/or the medical image content in the displayed image. For instance, a user may select a configuration where the co-registered image 1100 is presented as a blend of the visible light image content and the medical image content, such as a blend of 80% visible light image content and 20% medical image content. Other blending combinations are within the scope of the present disclosure, such as 0% visible light image content and 100% medical image content, 100% visible light image content and 0% medical image content, or any values therebetween for the visible light image content and the medical image content (e.g., 25% visible light image content and 75% medical image content, 50% visible light image content and 50% medical image content, 75% visible light image content and 25% medical image content, etc.).

Although the present disclosure has focused, in at least some respects, on radiopaque physical markers that are detectable via visible light imaging and radiography imaging, other types of physical markers may be utilized in accordance with the principles described herein. For instance, one or more physical markers may be placed within an imaging scene (e.g., including an imaging subject) that (i) are detectable via visible light imaging and (ii) include one or more radioisotopes that can be detected by, for example, nuclear medicine imaging systems (gamma camera, single-photon emission computerized tomography (SPECT) system, positron emission tomography (PET) system, etc.). For instance, multiple (e.g., three) physical markers that include one or more radioisotopes can be placed around a target structure such as a skin lesion (from the viewing perspective of the imaging system(s)), and the detected markers can be used to co-register a captured nuclear medicine image (e.g., nuclear scintigraphy image) with a captured visible light image.

In some implementations, the locations of the physical markers may be determined in 3D space (e.g., where the physical markers are imaged from multiple viewing angles), and the locations of the physical markers in 3D space may be used to co-register images (e.g., via camera reprojection).

Example Method(s) for Co-Registering Imagery of Different Modalities

The following discussion now refers to a number of methods (e.g., computer-implementable or system-implementable methods) and/or method acts that may be performed in accordance with the present disclosure. Although the method acts are discussed in a certain order and illustrated in a flow chart as occurring in a particular order, no particular ordering is required unless specifically stated, or required because an act is dependent on another act being completed prior to the act being performed. One will appreciate that certain embodiments of the present disclosure may omit one or more of the acts described herein.

Figure 12:
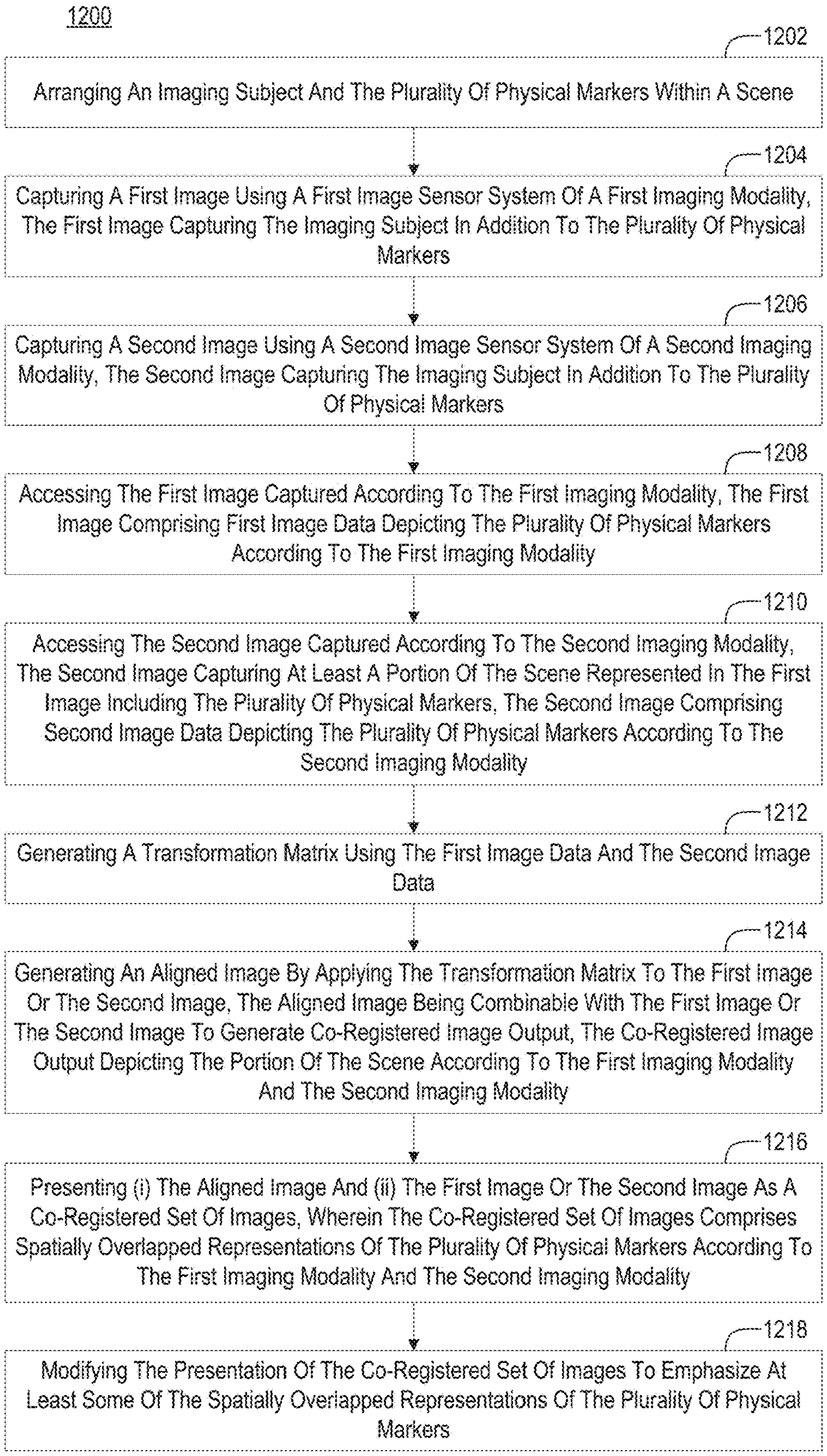
FIGS. 12, 13, and 14 illustrate example flow diagrams depicting methods for co-registering images of different modalities.
Figure 13:
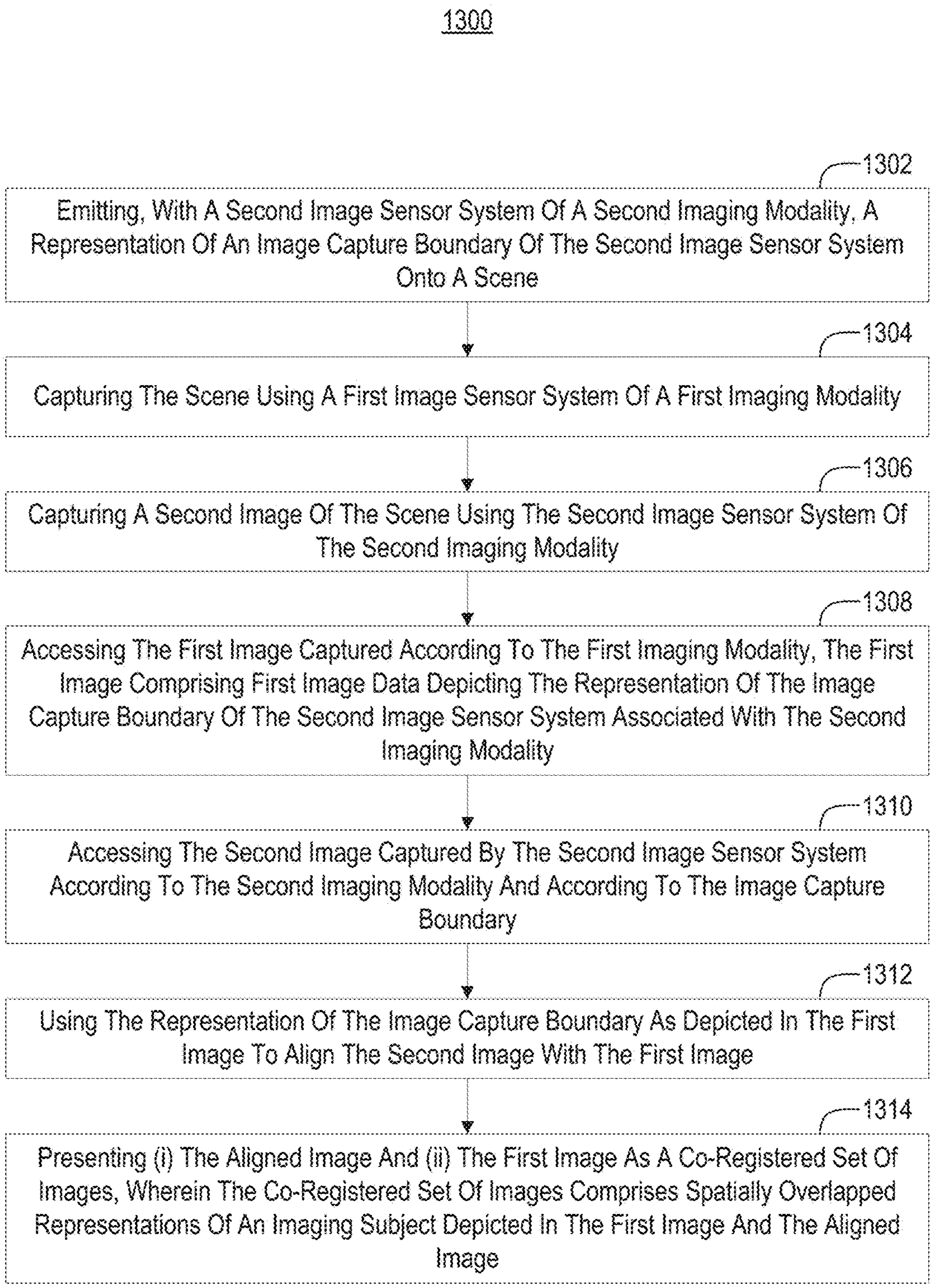
Figure 14:
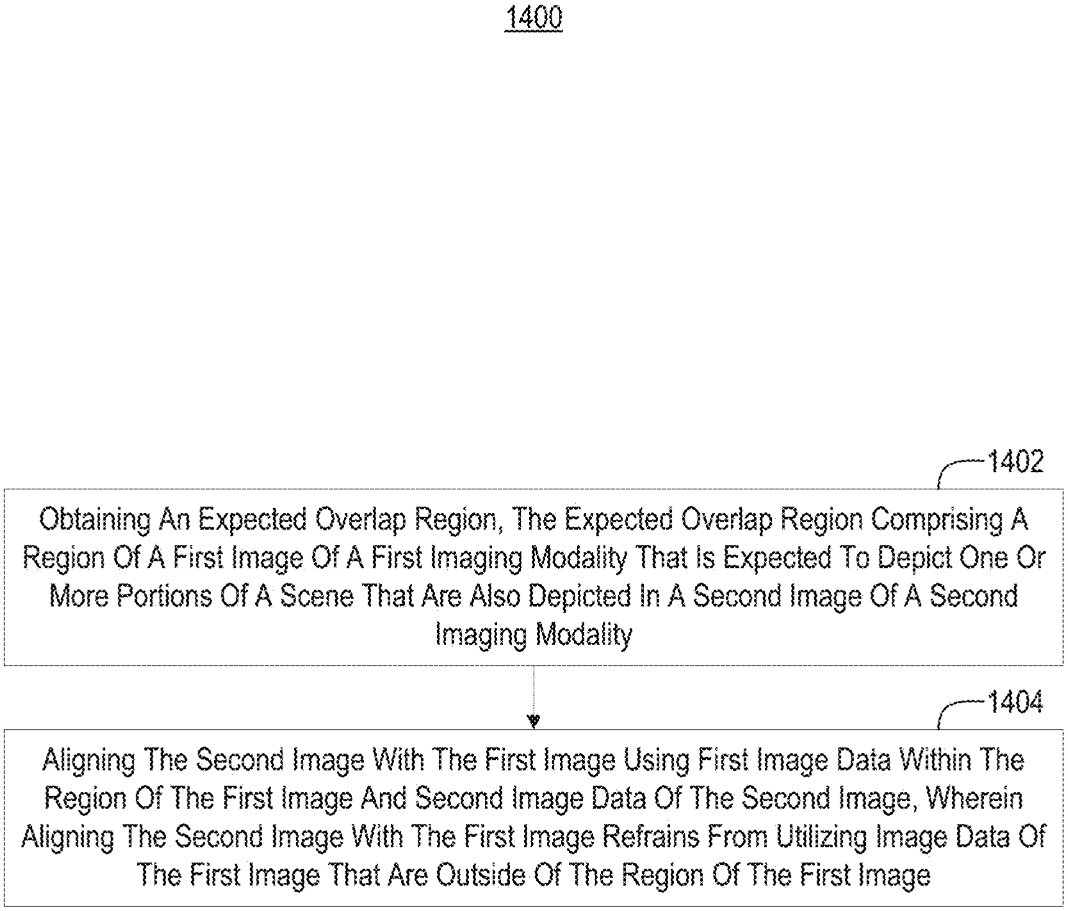

FIGS. 12, 13, and 14 illustrate example flow diagrams depicting methods for co-registering images of different modalities.

Act 1202 of flow diagram 1200 of FIG. 12 includes arranging an imaging subject and the plurality of physical markers within a scene. In some instances, act 1202 is performed utilizing physical markers (e.g., physical markers 310), processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128.

Act 1204 of flow diagram 1200 includes capturing a first image using a first image sensor system of a first imaging modality, the first image capturing the imaging subject in addition to the plurality of physical markers. In some instances, act 1204 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128.

Act 1206 of flow diagram 1200 includes capturing a second image using a second image sensor system of a second imaging modality, the second image capturing the imaging subject in addition to the plurality of physical markers. In some instances, act 1206 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128.

Act 1208 of flow diagram 1200 includes accessing the first image captured according to the first imaging modality, the first image comprising first image data depicting the plurality of physical markers according to the first imaging modality. In some instances, act 1208 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128. In some instances, the first imaging modality comprises a visible light imaging modality. In some implementations, the plurality of physical markers comprises a plurality of radiopaque physical markers that are visible in imagery of the first imaging modality and imagery of the second imaging modality.

Act 1210 of flow diagram 1200 includes accessing the second image captured according to the second imaging modality, the second image capturing at least a portion of the scene represented in the first image including the plurality of physical markers, the second image comprising second image data depicting the plurality of physical markers according to the second imaging modality. In some instances, act 1210 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128. In some instances, the second imaging modality comprises a medical imaging modality. In some implementations, the second imaging modality comprises a radiography imaging modality.

Act 1212 of flow diagram 1200 includes generating a transformation matrix using the first image data and the second image data. In some instances, act 1212 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128.

Act 1214 of flow diagram 1200 includes generating an aligned image by applying the transformation matrix to the first image or the second image, the aligned image being combinable with the first image or the second image to generate co-registered image output, the co-registered image output depicting the portion of the scene according to the first imaging modality and the second imaging modality. In some instances, act 1214 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128.

Act 1216 of flow diagram 1200 includes presenting (i) the aligned image and (ii) the first image or the second image as a co-registered set of images, wherein the co-registered set of images comprises spatially overlapped representations of the plurality of physical markers according to the first imaging modality and the second imaging modality. In some instances, act 1216 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128.

Act 1218 of flow diagram 1200 includes modifying the presentation of the co-registered set of images to emphasize at least some of the spatially overlapped representations of the plurality of physical markers (e.g., as demonstrated in FIG. 11). In some instances, act 1218 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128.

Act 1302 of flow diagram 1300 of FIG. 13 includes emitting, with a second image sensor system of a second imaging modality, a representation of an image capture boundary of the second image sensor system onto a scene. In some instances, act 1302 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128. In some instances, the second imaging modality comprises a medical imaging modality. In some implementations, the second imaging modality comprises a radiography imaging modality, and the second image sensor system emits visible light onto the scene indicating the representation of the image capture boundary Act 1304 of flow diagram 1300 includes capturing the scene using a first image sensor system of a first imaging modality. In some instances, act 1304 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128. In some instances, the first imaging modality comprises a visible light imaging modality.

Act 1306 of flow diagram 1300 includes capturing a second image of the scene using the second image sensor system of the second imaging modality. In some instances, act 1306 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128.

Act 1308 of flow diagram 1300 includes accessing the first image captured according to the first imaging modality, the first image comprising first image data depicting the representation of the image capture boundary of the second image sensor system associated with the second imaging modality. In some instances, act 1308 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128.

Act 1310 of flow diagram 1300 includes accessing the second image captured by the second image sensor system according to the second imaging modality and according to the image capture boundary. In some instances, act 1310 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128.

Act 1312 of flow diagram 1300 includes using the representation of the image capture boundary as depicted in the first image to align the second image with the first image. In some instances, act 1312 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128. In some instances, using the representation of the image capture boundary as depicted in the first image to align the second image with the first image comprises generating an aligned image by transforming the second image to cause an image boundary of the second image to align with the representation of the image capture boundary as depicted in the first image.

Act 1314 of flow diagram 1300 includes presenting (i) the aligned image and (ii) the first image as a co-registered set of images, wherein the co-registered set of images comprises spatially overlapped representations of an imaging subject depicted in the first image and the aligned image. In some instances, act 1314 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128.

Act 1402 of flow diagram 1400 of FIG. 14 includes obtaining an expected overlap region, the expected overlap region comprising a region of a first image of a first imaging modality that is expected to depict one or more portions of a scene that are also depicted in a second image of a second imaging modality. In some instances, act 1402 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128. In some instances, the first imaging modality comprises a visible light imaging modality. In some implementations, the second imaging modality comprises a medical imaging modality.

In some implementations, the expected overlap region is based upon depth information indicating a distance between one or more objects in the scene and (i) a first image sensor system for capturing the first image and/or (ii) a second image sensor system for capturing the second image. In some instances, the expected overlap region is based upon an offset between the first image sensor system and the second image sensor system. In some instances, the expected overlap region is based upon field of view information indicating a field of view associated with the first image sensor system and the second image sensor system.

Act 1404 of flow diagram 1400 includes aligning the second image with the first image using first image data within the region of the first image and second image data of the second image, wherein aligning the second image with the first image refrains from utilizing image data of the first image that are outside of the region of the first image. In some instances, act 1404 is performed utilizing processor(s) 102, storage 104, sensor(s) 110, I/O system(s) 118, communication system(s) 120, and/or other components of radiography system(s) 122, MRI system(s) 124, ultrasound system(s) 126, server(s) 132, and/or other system(s) 128. In some implementations, aligning the second image with the first image comprises maximizing mutual information between the region of the first image and at least a portion of the second image.

In some instances, aligning the second image with the first image comprises (i) detecting one or more structures within the region of the first image, (ii) detecting one or more corresponding structures within the second image, (iii) generating a transformation matrix using the one or more structures and the one or more corresponding structures, and (iv) aligning the second image using the transformation matrix. In some implementations, the one or more structures comprise one or more physical markers placed within the scene in preparation for an imaging session of an imaging subject within the scene. The one or more physical markers may be detectable according to the first imaging modality and the second imaging modality. In some implementations, the one or more structures comprise one or more medical components associated with an imaging subject within the scene. The one or more medical components may be detectable according to the first imaging modality and the second imaging modality.

ABBREVIATED LIST OF DEFINED TERMS

To assist in understanding the scope and content of the foregoing and forthcoming written description and appended claims, a select few terms are defined directly below.

The terms "physician", "clinician", "radiologist", and "technologist" as used herein generally refer to any licensed and/or trained person prescribing, administering, or overseeing the diagnosis and/or treatment of a patient or who otherwise tends to the wellness of a patient. This term may, when contextually appropriate, include any licensed medical professional, such as a physician (e.g., Medical Doctor, Doctor of Osteopathic Medicine, etc.), a physician's assistant, a nurse, a medical imaging technician, a dentist, a chiropractor, etc. and includes any physician specializing in a relevant field (e.g., radiology).

The term “patient” generally refers to any animal, for example a mammal, under the care of a healthcare provider, as that term is defined herein, with particular reference to humans under the care of a primary care physician, oncologist, surgeon, or other relevant medical professional. For the purpose of the present application, a “patient” may be interchangeable with an “individual” or “person.” In some embodiments, the individual is a human patient.

Additional Details Related to Computing Systems

Disclosed embodiments may comprise or utilize a special purpose or general-purpose computer including computer hardware, as discussed in greater detail below. Disclosed embodiments also include physical and other computer-readable media for carrying or storing computer-executable instructions and/or data structures. Such computer-readable media can be any available media that can be accessed by a general-purpose or special-purpose computer system. Computer-readable media that store computer-executable instructions in the form of data are one or more “physical computer storage media” or “hardware storage device(s).” Computer-readable media that merely carry computer-executable instructions without storing the computer-executable instructions are “transmission media.” Thus, by way of example and not limitation, the current embodiments can comprise at least two distinctly different kinds of computer-readable media: computer storage media and transmission media.

Computer storage media (aka “hardware storage device”) are computer-readable hardware storage devices, such as RAM, ROM, EEPROM, CD-ROM, solid state drives (“SSD”) that are based on RAM, Flash memory, phase-change memory (“PCM”), or other types of memory, or other optical disk storage, magnetic disk storage or other magnetic storage devices, or any other medium that can be used to store desired program code means in hardware in the form of computer-executable instructions, data, or data structures and that can be accessed by a general-purpose or special-purpose computer.

A “network” is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry program code in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a “NIC”), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Disclosed embodiments may comprise or utilize cloud computing. A cloud model can be composed of various characteristics (e.g., on-demand self-service, broad network access, resource pooling, rapid elasticity, measured service, etc.), service models (e.g., Software as a Service (“SaaS”), Platform as a Service (“PaaS”), Infrastructure as a Service (“IaaS”), and deployment models (e.g., private cloud, community cloud, public cloud, hybrid cloud, etc.).

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, wearable devices, and the like. The invention may also be practiced in distributed system environments where multiple computer systems (e.g., local and remote systems), which are linked through a network (either by hardwired data links, wireless data links, or by a combination of hardwired and wireless data links), perform tasks. In a distributed system environment, program modules may be located in local and/or remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Application-specific Standard Products (ASSPs), System-on-a-chip systems (SOCs), Complex Programmable Logic Devices (CPLDs), central processing units (CPUs), graphics processing units (GPUs), and/or others.

As used herein, the terms “executable module,” “executable component,” “component,” “module,” or “engine” can refer to hardware processing units or to software objects, routines, or methods that may be executed on one or more computer systems. The different components, modules, engines, and services described herein may be implemented as objects or processors that execute on one or more computer systems (e.g., as separate threads).

One will also appreciate how any feature or operation disclosed herein may be combined with any one or combination of the other features and operations disclosed herein. Additionally, the content or feature in any one of the Figures may be combined or used in connection with any content or feature used in any of the other Figures. In this regard, the content disclosed in any one figure is not mutually exclusive and instead may be combinable with the content from any of the other Figures.

CONCLUSION

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatuses disclosed herein may be made without departing from the scope of the disclosure or of the invention. Thus, while various aspects and embodiments have been disclosed herein, other aspects and embodiments are contemplated. All changes that come within the meaning and range of equivalency of the claims are to be embraced within their scope.

What is claimed is:

1. A system for facilitating co-registration of imagery of different modalities, the system comprising:

a first image sensor system configured to capture imagery of a first imaging modality;

a second image sensor system configured to capture imagery of a second imaging modality;

one or more processors; and one or more hardware storage devices that store instructions that are executable by the one or more processors such that the system is configurable to:

capture, via the first image sensor system, a first image of the first imaging modality;

capture, via the second image sensor system, a second image of the second imaging modality;

obtain an expected overlap region, the expected overlap region comprising a region of the first image that is expected to depict one or more portions of a scene that are also depicted in the second image, wherein the expected overlap region is based on an offset between the first image sensor system and the second image sensor system in 3D space; and process, via the one or more processors, first image data within the region of the first image and second image data of the second image to align the second image with the first image, wherein aligning the second image with the first image refrains from utilizing image data of the first image that are outside of the region of the first image.

2. The system of claim 1, wherein the expected overlap region is further based upon:

depth information indicating a distance between one or more objects in the scene and (i) the first image sensor system and/or (ii) the second image sensor system.

3. The system of claim 1, wherein the expected overlap region is further based upon:

field of view information indicating a field of view associated with the first image sensor system and the second image sensor system.

4. The system of claim 1, wherein the expected overlap region is further based upon a representation of an image capture boundary of the second image sensor system, the representation of the image capture boundary being depicted in the first image, the representation of the image capture boundary being emitted by the second image sensor system onto the scene.

5. The system of claim 1, wherein aligning the second image with the first image comprises maximizing mutual information between the region of the first image and at least a portion of the second image.

6. The system of claim 1, wherein aligning the second image with the first image comprises:

detecting one or more structures within the region of the first image;

detecting one or more corresponding structures within the second image that correspond to the one or more structures;

generating a transformation matrix using the one or more structures and the one or more corresponding structures; and aligning the second image using the transformation matrix.

7. The system of claim 6, wherein the one or more structures comprise one or more physical markers placed within the scene in preparation for an imaging session of an imaging subject within the scene, the one or more physical markers being detectable according to the first imaging modality and the second imaging modality.

8. The system of claim 6, wherein the one or more structures comprise one or more medical components associated with an imaging subject within the scene, the one or more medical components being detectable according to the first imaging modality and the second imaging modality.

9. A system for facilitating co-registration of imagery of different modalities, the system comprising:

a first image sensor system configured to capture imagery of a first imaging modality;

a second image sensor system configured to capture imagery of a second imaging modality;

one or more processors; and one or more hardware storage devices that store instructions that are executable by the one or more processors such that the system is configurable to:

capture, via the first image sensor system, a first image of the first imaging modality;

capture, via the second image sensor system, a second image of the second imaging modality;

obtain an expected overlap region, the expected overlap region comprising a region of the first image that is expected to depict one or more portions of a scene that are also depicted in the second image, wherein the expected overlap region is based on a representation of an image capture boundary of the second image sensor system, the representation of the image capture boundary being depicted in the first image, the representation of the image capture boundary being emitted by the second image sensor system onto the scene; and process, via the one or more processors, first image data within the region of the first image and second image data of the second image to align the second image with the first image, wherein aligning the second image with the first image refrains from utilizing image data of the first image that are outside of the region of the first image.

10. The system of claim 9, wherein the expected overlap region is based on an offset between the first image sensor system and the second image sensor system in 3D space.

11. The system of claim 10, wherein the expected overlap region is further based on depth information indicating a distance between one or more objects in the scene and (i) the first image sensor system and/or (ii) the second image sensor system.

12. The system of claim 10, wherein the expected overlap region is further based on field of view information indicating a field of view associated with the first image sensor system and the second image sensor system.

13. The system of claim 9, wherein aligning the second image with the first image comprises maximizing mutual information between the region of the first image and at least a portion of the second image.

14. The system of claim 9, wherein aligning the second image with the first image comprises:

detecting one or more structures within the region of the first image;

detecting one or more corresponding structures within the second image that correspond to the one or more structures;

generating a transformation matrix using the one or more structures and the one or more corresponding structures; and aligning the second image using the transformation matrix.

15. The system of claim 14, wherein the one or more structures comprise one or more physical markers placed within the scene in preparation for an imaging session of an imaging subject within the scene, the one or more physical markers being detectable according to the first imaging modality and the second imaging modality.

16. The system of claim 14, wherein the one or more structures comprise one or more medical components associated with an imaging subject within the scene, the one or more medical components being detectable according to the first imaging modality and the second imaging modality.

17. A system for facilitating co-registration of imagery of different modalities, the system comprising:

a first image sensor system configured to capture imagery of a first imaging modality;

a second image sensor system configured to capture imagery of a second imaging modality;

one or more processors; and one or more hardware storage devices that store instructions that are executable by the one or more processors such that the system is configurable to:

capture, via the first image sensor system, a first image of the first imaging modality;

capture, via the second image sensor system, a second image of the second imaging modality;

obtain an expected overlap region, the expected overlap region comprising a region of the first image that is expected to depict one or more portions of a scene that are also depicted in the second image; and process, via the one or more processors, first image data within the region of the first image and second image data of the second image to align the second image with the first image, wherein aligning the second image with the first image refrains from utilizing image data of the first image that are outside of the region of the first image, wherein aligning the second image with the first image comprises:

detecting one or more structures within the region of the first image, the one or more structures being detectable according to the first imaging modality and the second imaging modality, wherein the one or more structures comprise (i) one or more physical markers placed within the scene in preparation for an imaging session of an imaging subject within the scene, or (ii) one or more medical components associated with an imaging subject within the scene;

detecting one or more corresponding structures within the second image that correspond to the one or more structures;

generating a transformation matrix using the one or more structures and the one or more corresponding structures; and aligning the second image with the first image using the transformation matrix.

18. The system of claim 17, wherein the expected overlap region is based on an offset between the first image sensor system and the second image sensor system in 3D space.

19. The system of claim 18, wherein the expected overlap region is further based on depth information indicating a distance between one or more objects in the scene and (i) the first image sensor system and/or (ii) the second image sensor system.

20. The system of claim 18, wherein the expected overlap region is further based on field of view information indicating a field of view associated with the first image sensor system and the second image sensor system.

* * * * *